United States Patent [19]

Kung et al.

[11] Patent Number: 5,436,319
[45] Date of Patent: Jul. 25, 1995

[54] CELL FREE T CELL ANTIGEN RECEPTOR BETA CHAIN AND ITS CLINICAL UTILITIES

[75] Inventors: Patrick C. Kung, Cambridge; Stephen H. Ip, Framingham; Michael C. Brown, Wayland, all of Mass.

[73] Assignee: T Cell Sciences, Inc., Cambridge, Mass.

[21] Appl. No.: 312,167

[22] Filed: Sep. 26, 1994

Related U.S. Application Data

[63] Continuation of Ser. No. 129,007, Sep. 29, 1993, abandoned, which is a continuation of Ser. No. 929,613, Aug. 13, 1992, abandoned, which is a continuation of Ser. No. 582,041, Sep. 12, 1990, abandoned, which is a continuation of Ser. No. 239,048, Aug. 30, 1988, abandoned, which is a continuation of Ser. No. 935,879, Dec. 1, 1986, abandoned, which is a continuation-in-part of Ser. No. 804,289, Dec. 3, 1985, Pat. No. 4,845,026.

[51] Int. Cl.$^6$ ............................................. C07K 14/725
[52] U.S. Cl. ................................... 530/350; 530/830; 435/70.1
[58] Field of Search ............ 530/350, 387.1, 388.2, 530/388.22; 435/70.1

[56] References Cited

U.S. PATENT DOCUMENTS

| | | | |
|---|---|---|---|
| 4,707,443 | 11/1987 | Nelson et al. | 435/7.94 |
| 4,713,332 | 12/1987 | Mak | 435/69.1 |
| 4,845,026 | 7/1989 | Kung et al. | 435/5 |
| 4,873,190 | 10/1989 | Saito et al. | 435/172.3 |
| 4,874,845 | 10/1989 | Saito et al. | 530/395 |

OTHER PUBLICATIONS

J. Kappler et al. Cell 35:295–302 1983.
S. M. Hedrick et al. Nature 308:149 1984.
K. Haskins et al. J. Exp. Med. 157:1149–1169 1983.
O. Acuto et al. Cell 34:717–726 1983.
L. E. Samelson et al. Immunol. Rev. 81:131 1984.
B. W. McIntyre et al. Cell 34:739–46 1983.
A W Boylston et al. Eur. J. Immunol. 14:273–275 1984.
Ferguson and Iverson, 1986, Isolation And Character-
(List continued on next page.)

*Primary Examiner*—Garnette D. Draper
*Assistant Examiner*—Lorraine M. Spector
*Attorney, Agent, or Firm*—Banner & Allegretti, Ltd.

[57] ABSTRACT

Cell-free or released T cell antigen receptors, immunoassays which allow the detection of the released T cell antigen receptor in cell culture supernatants, cell lysates, and biological fluids, as well as diagnostic and therapeutic compositions and methods for monitoring and treating certain diseases or disorders which elicit or involve a T cell response are described. The released T cell antigen receptors described herein differ from the cell membrane bound antigen receptors and appear to exist in a variety of forms, some of which may be complexed with other T cell determinants such as the T3 antigen. Despite the size heterogeneity of the released T cell antigen receptors or receptor/complexes, these may be reliably identified using anti-receptor antibodies, including, but not limited to, anti-major framework, anti-minor frarmework and anti-clonotypic antibodies which define particular epitopes of the released T cell receptor or receptor/complex. The immunoassays described herein may be used to test for the presence of the released receptor or receptor/complex in biological samples and may be used to diagnose or monitor patients with disorders or diseases that elicit or involve T cell response who exhibit elevated serum level of the receptor or receptor/complex. In addition, the cell free T cell antigen receptors themselves may be used diagnostically and/or therapeutically for diseases or conditions that are not easily addressed using immunoglobulins.

8 Claims, 2 Drawing Sheets

OTHER PUBLICATIONS ization Of An Antigen-Specific Suppressor Inducer Molecule From Serum Of Hyperimmune Mice By Using A Monoclonal Antibody, J. Immunol. 136:2896–2903.

Schmidt, et al., 1986, Expression OF The NKTa Clonotype In A Series OF Human Natural Killer Clones With Identical Cytotoxic Specificity, J. Exp. Med 163:812–825.

Oettgen, et al., 1986, A T3-Like Protein Complex Associated With The Antigen Receptor On Murine T Cells, Nature 320:272–275.

Lanier, et al., Human Natural Killer Cells Isolated From Peripheral Blood Do Not Rearrange T Cell Antigen Receptor $\beta$ Chain Genes, J. Exp. Med. 163:209–214 1986.

Samelson, et al., 1985, Identification Of The Components Of The Murine T Cell Antigen Receptor Complex, Cell 43:223–231.

Suzuki, et al., 1985, Detection Of Antigen-Specific Suppressor T Cell Factor By Sandwich Radioimmunoassay Using Two Monoclonal Antibodies With Different Specificities, Int. Archs. Allergy. Appl. Immun. 77:300–307.

Yanagi, et al., 1985, Gene Rearrangement In Cells With Natural Killer Activity And Expression Of The $\beta$-Chain Of The T-Cell Antigen Receptor, Nature 314:631–633.

Taniguchi and Sumida, 1985, "1-J" As An Idiotypic Marker On The Antigen-Specific Suppressor T Cell Factor, Immunol. Rev. 83:125–150.

Reinherz, et al., 1984, Clonotypic Surface Structure On Human T Lymphocytes: Functional And Biochemical Analysis Of The Antigen Receptor Complex, Immunol. Rev. 81:95–129.

Hercend, et al., 1983, Identification Of A Clonally Restricted 90 kD Heterodimer On Two Human Cloned Natural Killer Cell Lines, J. Exp. Med. 158:1547–1560.

Tada and Okimura, 1979, The Rode Of Antigen-Specific T Cell Factors In The Immune Response, Adv. Immunol. 28:1–27.

CELL FREE T CELL ANTIGEN RECEPTOR BETA CHAIN AND ITS CLINICAL UTILITIES

This is a continuation of application Ser. No. 08/129,007, filed Sep. 29, 1993, now abandoned, which is a continuation of application Ser. No. 07/929,613, filed Aug. 13, 1992, now abandoned, which is a continuation of Ser. No. 07/582,041, filed Sep. 12, 1990, now abandoned, which is a continuation of Ser. No. 07/239,048, filed Aug. 30, 1988, now abandoned, which is a continuation of Ser. No. 06/935,879, filed Dec. 1, 1986, now abandoned, which is a continuation-in-part of Ser. No. 06/804,289, filed Dec. 3, 1985, which is now U.S. Pat. No. 4,845,026.

1. INTRODUCTION

The present invention relates to cell free T cell antigen receptors and their use in diagnostics and therapeutics. The cell free T cell antigen receptors defined and described herein are released from T cells lines in culture and in individuals with disorders or diseases that involve T cell responses. These released receptors differ from the cellular membrane bound receptor and may be used therapeutically or diagnostically for certain T cell malignancies, and other diseases or disorders which elicit or involve T cell responses, including some infectious diseases, cancers, solid tumors, autoimmune diseases, allergies etc.

The invention also relates to methods for detecting the released T cell antigen receptor in cell culture supernatants, cell lysates and in human sera.

2. BACKGROUND OF THE INVENTION

The disclosures of the publications referenced within this application in their entirety are hereby incorporated by reference into this application in order to more fully describe the state of the art to which this invention pertains.

The primary cells of the immune system are the small white blood cells, called lymphocytes, derived from stem cells in the bone marrow. The differentiation of one class of lymphocytes is completed in the thymus gland. Accordingly, these lymphocytes are called T cells.

T cells circulate through the blood and lymphatic vessels of the body and are able to detect and react against foreign invaders, allergens, tumors and auto antigens. Despite their uniform morphology observed under the microscope, T cells consist of a heterogeneous population of three major subsets: the cytotoxic cells that destroy virus-infected cells; and two subsets, designated helper and suppressor cells, which regulate the antibody producing B cells.

A T cell clone is a T cell from which a population of identical T cells is derived by clonal expansion. The molecular nature of the T cell antigen receptor was reported in the early 1980's by several research groups (Allison, et al., 1982, J. Immunol. 129: 2293-2300; Kappler, et al., 1983, Cell 35: 295-302; Acuto, et al., 1983, J. Exp. Med 158: 1368-1373. As shown in these reports the T cell antigen receptor is a heterodimeric glycoprotein composed of two glycosylated polypeptides, one of which is designated the alpha chain and the other of which is designated the beta chain. A T cell antigen receptor is normally present on the surface of each T cell. Each T cell recognizes a single antigenic determinant in association with a protein of a major histocompatibility complex (MHC protein). All T cells derived from a T cell clone contain identical T cell antigen receptors and recognize the same antigenic determinant in association with the same MHC protein.

The alpha and beta chains of the T cell antigen receptor of a T cell clone are each composed of a unique combination of domains designated variable (V), diversity (D), joining (J), constant (C) (Siu, et al., 1984, Cell 37: 393; Yanagi, et al., 1985, Proc. Natl. Acad. Sci. U.S.A., 82: 3430), and hypervariable (Patten et al., 1984, Nature 312: 40; Becker et al., 1985, Nature 317: 430). In each T cell clone the combination of V, D and J domains of both the alpha and the beta chains participates in antigen recognition in a manner which is uniquely characteristic of that T cell clone and defines a unique binding site, also known as the idiotype of the T cell clone. In contrast, the C domain does not participate in antigen binding.

In addition to the alpha and beta chains, a third distinct gene, designated T cell receptor gamma gene, has been isolated. The sequence and organization of the gamma gene are similar to immunoglobulin genes and genes for the alpha and beta chain of the T cell antigen receptor (Hayday, et al., 1985 Cell 40: 259-269). The gamma gene is expressed only in T cells. Tonegawa and coworkers suggest that T cell antigen receptors of some T cells are made up of a gamma chain and a beta chain (S. Tonegawa, The Molecules of the Immune System, Scientific American, pp. 122-131, October, 1985).

The alpha and beta chains of the T cell antigen receptor of a T cell clone also define a plurality of antigenic determinants which can be recognized by antibodies directed to the antigen receptor. An antibody which reacts solely with the T cell clone or inhibits antigen binding only to the antigen receptor of the T cell clone against which it is raised is defined to be anti-clonotypic (Kappler, et al., 1983, Cell 35: 295-302; Boylston, et al., 1984, Eur. J. Immunol. 14: 273; Acuto, et al., 1985, J. Exp. Med. 161: 1326). If an antigenic determinant defined by the alpha or beta chains, or both, is present on the surface of, or associated with, a relatively limited number of T cell clones, the determinant is designated a minor framework determinant of the T cell antigen receptor (Acuto, et al., 1985, J. Exp. Med. 161: 1326; Bigler, et al., 1985, J. Exp. Med. 161: 1450). If an antigenic determinant defined by the alpha or beta chain, or both, is present on the surface of, or associated with, a relatively large number or all T cell clones, the determinant is designated a major framework determinant of the T cell antigen receptor (Brenner, et al., 1984, J. Exp. Med. 160: 541; Spits et al., 1985, J. Immunol. 135: 1922).

Natural Killer (NK) cells, although lacking most of the surface differentiation antigens associated with the three major subsets of T cells, have been confirmed as members of the T cell lineage and are considered by many to be a subset of T cells. NK cells are characterized by their ability to mediate direct cytotoxicity against specific target cells, e.g. cancer cells, without apparent prior immunization (Ritz, et al., 1985, Science 228: 1540; Robertson, 1985, Nature 317: 768). It has been observed that some NK cells have on their surfaces a heterodimeric receptor capable of antigen recognition without specific MHC protein associations. For purposes of this application, unless otherwise stated, all references to antigen receptors shall include heterodimeric antigen receptors derived from the surface of T cells and NK cells.

It has been suggested that the T cell antigen receptor is noncovalently associated with the T3 protein complex on the membrane (Borst, et al., 1983, J. Biol. Chem. 258: 5135). The T3 protein complex is composed of three distinct membrane associated polypeptide chains known as T3-gamma, T3-delta and T3-epsilon (Van den Elsen, et al., 1985, Proc. Natl. Acad. Sci. U.S.A. 82: 2920). This T3 protein-antigen receptor association can be demonstrated by immunoprecipitation studies with antibodies against the T3 protein complex and by comodulation or mutant studies in which the antigen receptor and the T3 protein complex may co-disappear or co-appear on the membrane (Ohashi, et al., 1985, Nature 316: 606).

Heretofore the measurement of T cell antigen receptors has been limited to the detection of T cell-associated antigen receptors by a variety of immunological techniques involving monoclonal antibodies against the antigen receptor. Such measurements have been routinely accomplished by binding fluorescence conjugated monoclonal antibodies to T cells followed by cellular analysis with a fluorescent-activated cell sorter or similar flow cytometer (Acuto, et al., 1985, J. Exp. Med. 16: 1326). Such cell analysis provides information about the percent of T cells expressing the receptor in a given sample, however the accuracy and reliability of such routine analysis is limited to 1–2% or more of positive cells in a sample using existing flow cytometers. Furthermore the cell analysis is tedious and often requires fresh, live cells and a skilled, dedicated operator.

The molecular mechanism of T cell antigen receptor-antigen interaction is a subject of intensive investigation (Robertson, 1985, Nature 317: 768). It has been shown (Watts, et al., 1985, Proc. Natl. Acad. Sci. U.S.A. 82: 5480) that T cell clones are capable of binding membrane bound antigens associated with MHC proteins. Rao, et al. (Rao, et al., 1984, Cell 36: 879) reported however that some antigens can bind to the antigen reactive T cell clones in the absence of a MHC protein. In a recent report (Bialy, 1985, Biotechnology 3: 858) on ligand binding to the T cell antigen receptor, recombinant DNA techniques were used to prepare a hybrid molecule with T cell antigen receptor regions contained within immunoglobulin frameworks. However, no immunological reactivities against the hybrid molecules were described therein.

Between 1975–1981, a series of papers were published on the characterization of "T cell antigen receptors" in mouse and rat systems (Krawinkel, et al., 1976, Cold Spr. Harb. Symp. Quant. Biol. 4: 285; Binz and Wigzell, 1976, Cold Spr. Harb. Symp. Quant. Biol. 4: 275; Binz and Wigzell, 1981, J. Exp. Med. 154: 1261). These "T cell antigen receptors" are not the "T cell antigen receptor" described herein (see Allison, et al., 1982, J. Immunol. 129: 2293–2300; Kappler, et al., 1983, Cell 35: 295–302; Acuto, et al., 1983, J. Exp. Med 158: 1368–1373; Hayday, et al., 1985, Cell 40: 259–269; Kranz, et al., 1985, Science 227: 941). Krawinkel, et al., 1976, Cold Spr. Harb. Symp. Quant. Biol. 4: 285; Binz and Wigzell, 1976, Cold Spr. Harb. Symp. Quant. Biol. 4: 275 and Binz and Wigzell, 1981, J. Exp. Med. 154: 1261, describe a protein, designated "T cell antigen receptor", with a molecular weight of approximately 150,000–180,000 daltons. This "antigen receptor" is further characterized as a dimer with a protein subunit having a molecular weight of about 70,000 daltons. The chromosomal location of this "antigen receptor's" variable region in mice is on chromosome 12 (Binz and Wigzell, 1981, J. Exp. Med. 154: 1261). The T cell antigen receptor described within this application has a molecular weight of about 90,000 daltons (Allison, et al., 1982, J. Immunol. 129: 2293–2300; Kappler, et al., 1983, Cell 35: 295–302; Acuto, et al., 1983, J. Exp. Med 158: 1368–1373). Furthermore, the subunit structures of this antigen receptor consist of heterodimeric glycosylated polypeptides, designated the alpha, beta, or gamma chains, having molecular weights in man of approximately 45,000 daltons, (Kappler, et al., 1983, Cell 35:295) 40,000 daltons, (id) and 55,000 daltons (Brenner, et al., 1986, Nature 322:145), respectively. The chromosomal locations of the variable regions in mice are: alpha, chromosome 14 (Kranz, et al., 1985, Science 227: 941); beta, chromosome 6 (Caccia, et al., 1984, Cell 37: 1091); and gamma, chromosome 13 (Kranz, et al., 1985, Science 227: 941).

In 1982, it was reported that the external shedding of the T3 protein by human T cell clones could be artificially induced by adding an anti-T3 protein antibody to these T cells in culture. However, no observation of the spontaneous shedding or release of T3 protein, in vivo or in vitro, was noted (Reinherz, et al., 1982, Cell 30: 735).

Fujimoto et al. (Fujimoto, et al., 1983, J. Exp. Med. 159: 752).developed an enzyme-linked immuno-absorbent assay (ELISA) for the detection of human T cell surface antigens in soluble form. When sera and culture supernatants from various cell lines were tested, Leu-2 antigen, but not Leu-1 or Leu-3, was found to be present. Applicants are also aware of the pending U.S. patent application, U.S. Ser. No. 724,897, filed Apr. 19, 1985 in the name of David Nelson et al., assigned to the U.S. Government and entitled "Soluble Interleukin-2 Receptor As A Disease Indicator And A Method of Assaying The Same." This patent application, based on the findings of Rubin et al. (Rubin, et al., 1985, J. Immunol. 135: 3172), concerns soluble or released Interleukin-2 Receptor, which is believed to interact with the T cell growth factor Interleukin-2. Applicants are also aware of U.S. Pat. No. 4,550,086 by Reinherz et al., which describes monoclonal antibodies that specifically bind to the "surface recognition structure" of T cells. However, neither the Fujimoto publication, the Nelson patent application, the Rubin publication nor the Reinherz patent discloses or teaches the existence of a cell free or released T cell antigen receptor, methods for detecting and measuring it in a biological fluid or methods for its diagnostic and therapeutic use.

3. SUMMARY OF THE INVENTION

The present invention is directed to cell-free T cell antigen receptors and their use in diagnosis and therapy of certain diseases or disorders which elicit or involve a T cell response. The invention is based, in part, upon a number of discoveries: (a) that certain T cell lines in culture spontaneously release their antigen receptors into the culture fluid (for example, during the log phase of growth); (b) that the released T cell antigen receptors can be produced by cells that never express a membrane-bound antigen receptor; (c) that in vivo, certain diseases or disorders which elicit or involve T cell responses (e.g., autoimmune disease, organ transplant/graft rejection, graft versus host disease, T cell malignancies, cancers, solid tumors, allergies, and certain infectious diseases) are characterized by the presence of specific released T cell antigen receptors in body fluids; (d) these released receptors exist in a variety of forms which differ from the cell membrane bound receptor species, and which may be complexed with other T cell determinants such as the T3 antigen; and (e) the invention is also based, in part, on the further discovery that the released T cell antigen receptor may be defined by particular anti-receptor antibodies despite the variation in form of the released receptor or released receptor/-complex; immunoassays are described herein which may be used to identify such released T cell antigen receptor molecules.

The cell free antigen receptors of the invention may comprise monomers, homodimers, or heterodimers of peptides or polypeptides related to the alpha, beta, gamma or delta chains or subunits of the T cell antigen receptor (see Section 3.1 infra for definitions) and include fragments and/or derivatives thereof which may or may not be complexed to another molecule, such as a T cell determinant.

The invention is also directed to diagnostic assays which are based upon the detection or quantitation of the cell free receptor or receptor/complex in patient samples. In patients afflicted with diseases or disorders that elicit or involve a T cell response, the T cell antigen receptor is released at a metabolic rate which differs from that of the normal condition, causing the released receptor to become accumulated in body fluids. As a result, an increased concentration of released receptor may be correlated with certain diseases. Rapid, sensitive and inexpensive methods are disclosed for determining the relative concentrations of released receptor in a body fluid; which may be useful for diagnosis and monitoring disease in a patient. Because the cell free receptors can be detected in body fluids which can be obtained via relatively non-invasive techniques, a particular advantage is obtained in the diagnosis of disorders or diseases which would normally require invasive biopsy procedures (e.g., rejected heart or kidney transplants, and the like), or which cannot be biopsied (e.g., inoperable or inaccessible tumors).

The invention is also directed to diagnostic and therapeutic compositions in which the released T cell antigen receptor is admixed with diagnostically or pharmaceutically acceptable carriers. These methods may be particularly useful in the diagnosis and therapy of diseases and disorders to which immunoglobulins do not readily react. It is well known that both T cells and B cells recognize antigens with specificity (S. Tonegawa, The Molecules of the Immune System, Scientific American, pp. 122–131, October, 1985; Robertson, 1985, Nature 317: 768). Although it is established that T cells, unlike B cells, usually recognize antigens in association with MHC proteins, it is not clear whether epitopes on an antigen which are recognizable by T cells or B cells are related. In a recent report, G. S. Bixler and M. Z. Atassi (Bixler and Atassi, 1985, Biotechnology 3: 47) concluded that the regions of a protein molecule recognized by B cells (antibody binding) may also be recognized by T cells. T cells, however, may recognize additional areas of the molecule to which no detectable antibody responses have thus far been observed. These data suggest that the unique aspect of T cell recognition is useful for detecting disease antigens in diagnostic and therapeutic applications (Bixler and Atassi, 1985, Biotechnology 3: 47). The existence of cell free T cell antigen receptors disclosed herein provides a novel source of reagents for these applications.

3.1. DEFINITIONS

As used herein the following terms will have the meanings indicted:

Anti-receptor Antibody: an antibody that reacts with an epitope of the T cell antigen receptor. Anti-receptor antibodies may comprise anti-clonotypic, anti-minor framework or anti-major framework antibodies.

Anti-clonotypic Antibody: an antibody that reacts solely with the T cell clone or which inhibits antigen binding only to the antigen receptor of the T cell clone against which the antibody was raised. In parent application Ser. No. 804,289, anti-clonotypic antibodies were defined as "anti-idiotypic" antibodies. This terminology has been modified herein in order to avoid confusion with anti-idiotypic antibodies that define the antigen combining site of immunoglobulins. Accordingly, the term "anti-clonotypic antibodies" as used herein describes antibodies that define the antigen combining site of a particular T cell antigen receptor.

Anti-minor Framework Antibody: an antibody that defines the minor framework determinant of the T cell antigen receptor which comprises alpha or beta chains, or both, which are present on the surface of or associated with a relatively limited number of T cell clones. In general, antibodies to minor framework determinants will recognize less than 20% of the peripheral T cells of a normal subject.

Anti-major Framework Antibody: an antibody that defines the major framework determinant of the T cell antigen receptor comprising the alpha chain or the beta chain, or both, which are present on the surface of or associated with a relatively large number or all T cell clones. In general, antibodies to major framework determinants will recognize at least 20% of the peripheral T cells of a normal subject.

Although the demarcation between being present on a relatively limited number of T cell clones and being present on a relatively large number or all T cell clones is not always precise, those skilled in the art to which this invention pertains fully understand and appreciate this demarcation and can readily classify most given antigenic determinants as being either a minor or a major framework determinant. For purposes of this application any antigenic determinant as to which those skilled in the art would not concur is defined to be a minor framework determinant.

Alpha and Beta Subunits or Chains: the alpha and beta subunits of the T cell antigen receptor have a relative molecular mass ($M_r$) of approximately 50,000 and 40,000 daltons, respectively. Genes that rearrange during T cell ontogeny and encode the beta subunit (Yanagi, et al., 1984, Nature 308:145–149; Hedrick et al., 1984 Nature 308:153–158) and alpha subunit (Chien et al., 1984, Nature 312:31–35; Saito et al., 1984, Nature 312:36–40; Sim et al., 1984, Nature 312:771–775) have been isolated either by substractive hybridization or by probing with oligonucleotides.

A unique feature of the human alpha, beta chains of the T cell antigen receptor was the observed comodulation (Meuer et al., 1983, J. Exp. Med. 157:705–719), coimmunoprecipitation (Reinherz et al., 1983, Proc. Natl. Acad. Sci. U.S.A. 80:4104–4108; Oettgen et al., 1984, J. Biol. Chem. 259:12039–12048) and required coexpression (Weiss & Stobo, 1984, J. Exp. Med.

160:1284-1299) of the alpha, beta molecules, with the T3 glycoprotein, which suggested that these two structures were related. Subsequently, the direct physical association of the two protein complexes was demonstrated by chemically cross-linking the alpha, beta molecules to the T3 glycoprotein and identifying the components of the cross-linked complex as the beta subunit and the T3 glycoprotein ($M_r 28,000$) subunit (Brenner et al., 1985, Cell 40:183-190). A T3 counterpart is similarly associated with murine alpha, beta T cell antigen receptor (Allison et al., 1985, Nature 314:107-109; Samelson & Schwartz, 1984, Immunol. Rev. 81:131-144).

Gamma and Delta Subunits or Chains: a third gene that rearranges in T cells, designated gamma, has been identified in mouse (Saito et al., 1984, Nature, 309:757-762; Kranz et al., 1985, Nature 313:752-755; Hayday et al., 1985, Cell 40:259-269) and in man (Lefranc et al., 1985, Nature 316:464-466; Murre, et al., 1985, Nature 316:549-552). However, there are major differences between the human and mouse gamma gene in terms of its genetic structure; for example, the cDNA of the human gamma gene indicates five potential sites for N-linked glycosylation in the gamma gene product, which contrasts with the notable absence of such sites in the murine gamma gene. Thus, the human gamma gene product will have a high molecular weight which is not predictable from its genetic sequence.

The gamma gene rearrangements occur in lymphocytes with suppressor-cytotoxic as well as helper phenotypes and may produce a large number of gamma chains. However, the function of the gamma gene is unknown. Furthermore, neither the protein encoded by the gamma gene nor its possible association with other structures (as occurs with alpha, beta adn T3 glycoproteins) have been defined. In humans, the multiple glycosylation sites render it impossible to predict with accuracy the nature and size of the gamma polypeptide structure. Recently, a 55 kd polypeptide has been putatively identified as the gamma subunit.

The delta T cell receptor polypeptide has a molecular weight of about 40,000 daltons and may form a T3 associated heterodimer with the gamma subunit. The gamma and delta subunits are more completely described in application Ser. Nos. 882,100 and 881,825 filed Jul. 3, 1986 and the following publication: Brenner et al., 1986, Nature 322:145-149 which are incorporated by reference herein in their entirety. These references also describe anti-framework antibodies that define these novel T3 associated polypeptides.

T3 Protein Complex: the T3 protein complex is composed of three distinct membrane associated polypeptide chains known as T3-gamma, T3-delta and T3-epsilon (Van den Elsen, et al., 1985, Proc. Natl. Acad. Sci. U.S.A. 82: 2920). This T3 protein-antigen receptor association can be demonstrated by immunoprecipitation studies with antibodies against the T3 protein complex and by comodulation or mutant studies in which the antigen receptor and the T3 protein complex may co-disappear or co-appear on the membrane (Ohashi, et al., 1985, Nature 316: 606).

As used herein, "T cell" defines cells derived from thymus lineage and which express T cell antigen receptor molecules.

5. DETAILED DESCRIPTION OF THE INVENTION

The present invention is directed to cell-free or released T cell antigen receptors, immunoassays which allow the detection of the released T cell antigen receptor in cell culture supernatants, cell lysates, and biological fluids, as well as diagnostic and therapeutic compositions and methods for monitoring and treating certain diseases or disorders which elicit or involve a T cell response.

The invention is based, in part, upon the initial discovery that certain T cell lines in culture spontaneously release particular antigen receptors into the culture fluid (for example, during the log phase of growth) and that cell free antigen receptors can be released from cells that never express the membrane bound form. The released T cell antigen receptors described herein differ from the cell membrane bound antigen receptors and appear to exist in a variety of forms, some of which may be complexed with other T cell determinants such as the T3 antigen.

The invention is also based, in part, upon another discovery that, despite the size heterogeneity of the released T cell antigen receptors or receptor/complexes, these may be reliably identified using anti-receptor antibodies, including, but not limited to, anti-major framework, anti-minor framework and anti-clonotypic antibodies which define particular epitopes of the released T cell receptor or receptor/complex. The anti-receptor antibodies can be used for the identification, isolation or purification of the cell free T cell antigen receptors. Combinations of these antibody molecules may be used in immunoassays described in more detail infra for detecting and identifying particular classes of cell free T cell antigen receptors of the invention.

The invention is also based, in part, upon the further discovery that under certain conditions in vivo specific T cell antigen receptors are released from T cells into the surrounding body fluid. Such conditions which result in the release of T cell antigen receptors in vivo include but are not limited to diseases or disorders that elicit or involve a T cell response, for example, autoimmune diseases, organ transplant/graft rejection, graft verses host disease, T cell malignancies, cancers, solid tumors, certain infectious diseases, allergies and the like. The immunoassays described herein may be used to test for the presence of the released receptor or receptor/complex in biological samples and may be used to diagnose or monitor patients with disorders or diseases that elicit or involve T cell responses who exhibit elevated serum levels of the receptor or receptor/complex. In addition, the cell free T cell antigen receptors themselves may be used diagnostically and/or therapeutically for diseases or conditions that are not easily addressed using immunoglobulins.

For purposes of clarity, the invention will be described in the subsections below in terms of (a) the nature of the cell free T cell antigen receptor; (b) the detection of cell free T cell antigen receptor; and (c) the use of the cell free T cell antigen receptor for the diagnosis, monitoring and therapy of diseases or disorders which elicit or involve T cell responses.

5.1. THE NATURE OF THE CELL-FREE T CELL ANTIGEN RECEPTOR

The cell free T cell antigen receptors of the invention comprise a population of molecules which demonstrates a considerable heterogeneity in size ranging from apparent molecular weights of about 180 kd to about 20 kd. The cell-free T cell antigen receptors of the invention may comprise monomers, homodimers, or heterodimers of peptides or proteins related to the alpha, beta, gamma or delta chains of the T cell antigen receptor (see Section 3.1 for definitions) including fragments and/or derivatives thereof which may or may not be complexed to another molecule such as a T cell determinant. The fragments or derivatives of the receptor molecules may be functional, i.e., capable of binding to an antigen associated with an MHC protein or an NK antigen receptor capable of binding to antigen. Such fragments of the cell free antigen receptors may include, but are not limited to fragments containing epitopes of the major or minor framework determinants, the clonotype of the molecule or the constant, variable, or hypervariable regions.

Despite this variety in molecular size and form, the cell free antigen receptors of the invention are sufficiently stable so that they can be definitively identified using anti-receptor antibodies that define epitopes on the cell free receptors. Examples of monoclonal antibodies and immunoassays which can be used to identify the cell free T cell antigen receptor are described more fully in Section 5.2. and the examples infra.

The cell free antigen receptors of the invention may be produced by purification from cells that release cell free receptors at high levels, by recombinant DNA technology or by chemical synthetic techniques. For example, the cell free receptors may be purified from a number of cells that release receptors including but not limited to T cells, T cell lines, NK cells, T cell-T cell hybridomas and host cells which have been genetically engineered to produce released receptors. We have discovered that the cell free form of the T cell antigen receptor may be purified from cultures of cells which contain a cytoplasmic T cell antigen receptor and release the cell free form but do not express the membrane bound form of the receptor. An example of such a cytoplasm-positive, membrane-negative cell line that releases the cell free form of the T cell antigen is the T cell line Molt 4. The cell free T cell antigen receptor of the invention may also be purified from T cell-T cell hybridoma cell lines which express and release the T cell antigen receptor. Such T cell hybridoma techniques are known in the art and may be used in accordance with this embodiment of the present invention (see, for example, Gallagher et al., 1986, J. Immunol. Methods 90: 57. Alternatively, recombinant DNA techniques can be used to genetically engineer cell transformants that produce the released receptors. To this end, nucleotide sequences that encode alpha, beta, gamma or delta chains of the T cell antigen receptor, or portions thereof, can be placed under the control of appropriate expression ,elements (promoters, enhancers, etc.) to produce recombinant DNA molecules which, when used to transform appropriate host cells, will direct the expression and release of the T cell antigen receptor or appropriate fragments thereof. Due to the degeneracy of the DNA code, these nucleotide sequences include derivatives and substitutions that result in silent changes in the translated amino acid chains.

Alternatively, the receptors may be produced by chemical synthetic methods. To this end the subunits which make up the monomers or dimers that form the cell free T cell antigen receptors can be synthesized by techniques known in the art (Merrifield, 1963, J. Am. Chem. Soc. 85:2149). These subunits may comprise amino acid sequences that are the same or substantially the same as all or portions of the sequences obtained for the alpha, beta, gamma and delta chains of the T cell antigen receptor, including but not limited to modifications and substitutions within the amino acid sequence that result in silent changes. Such modifications include substitutions of amino acid residues that have substantially equivalent acid/base properties and/or hydrophilicity/hydrophobicity properties.

Cell free antigen receptors may be purified using methods known in the art including but not limited to chromatographic techniques, electrophoretic techniques and immunological methods. Immunoaffinity techniques and chromatographic methods including HPLC (high performance liquid chromatography) are particularly useful for the purification of the cell free antigen receptor; see Section 5.2. infra which describes antibodies that could be used in such immunopurification schemes; see also FIG. 1 and FIG. 2 infra, as well as Siliciano et al., 1986, Cell 47:161-171 for examples of such purification methods.

The ability of the purified cell free antigen receptor to retain its stability and valency which enables the receptor to bind to its specific antigen is demonstrated by the examples herein and supported by recent data (see Siliciano et al., 1986, Cell 47: 161-171) which demonstrates the ability of T cell antigen receptors derived from cell lysates to bind to antigen.

5.2. DETECTION AND IDENTIFICATION OF THE CELL FREE T CELL ANTIGEN RECEPTOR

A number of anti-receptor antibodies, i.e., anti-major framework, anti-minor framework and anti-clonotypic, react specifically with the released or cell free T cell antigen receptor molecules, yet do not cross react with irrelevant cells or molecules. Such anti-receptor antibodies can be used to identify, purify, or isolate the cell free T cell antigen receptors of the invention as well as fragments and derivatives thereof, as defined in Section 5.1. Such immunoassays and/or immunoaffinity purification schemes may or may not include the use of additional antibodies that define epitopes of molecules that may be complexed to the cell free T cell antigen receptor.

The anti-major framework antibodies in general, probably define a part or all of the constant region of the cell free T cell antigen receptor and, thus, can be used to detect, isolate or purify a class of cell free T cell antigen receptors that share the particular constant region defined by the anti-major framework antibody. Although anti-minor framework antibodies may define portions of the constant region of the receptor molecule, in all likelihood there may be involvement of the variable region as well. As a result, the anti-minor framework antibodies may be used to identify, isolate or purify a smaller subset of the cell free T cell antigen receptors. Assuming the constant region of the cell free T cell antigen receptors determines the effector function or biological activity of the molecule, it is contemplated that the anti-framework antibodies can be used to identify, isolate or purify cell free T cell receptors of a particular class that exhibit a desired effector function.

By contrast to the anti-framework antibodies, the anti-clonotypic antibodies which define the antigen combining site of the cell free T cell antigen receptor probably bind to variable and hypervariable regions of the receptor molecule, and may be used to identify, isolate or purify cell free T cell antigen receptors which are specific for particular antigens regardless of their effector function.

Combinations of anti-receptor antibodies may be used to identify, isolate or purify cell free T cell antigen receptors that define a particular antigen and which possess or exhibit a particularly desirable effector function. For example, combinations of an anti-clonotypic antibody that defines the antigen combining site of interest with an anti-framework antibody that defines a subset of cell free receptors characterized by a desired effector function may be used to identify, isolate or purify the desired cell free receptor.

In order to identify or detect the cell free T cell antigen receptors of the invention, the anti-receptor antibodies may be used in any type of immunoassay including but not limited to competitive, noncompetitive, and "sandwich" immunoreactions which may be detected using any appropriate label such as radioisotopes, fluorescence, enzyme-substrate reactions, colorimetric dyes, immunoprecipitation, agglutination, complement fixation, and the like. Such immunoassays include but are not limited to radioimmunoassays, immunoradiometric assays, fluorescence immunoassays, enzyme-linked immunoassays, protein A immunoassays, immunodiffusion, immunoprecipitation, immunoelectrophoresis, complement fixation, agglutination assays, and the like.

Immunoassays for the detection of the cell free antigen receptor are described in the examples which utilize different combinations of the anti-receptor antibodies with or without other antibodies that define T cell determinants that may form complexes with the cell free receptors (such as the T3 antigen). In a particular embodiment, sandwich immunoassays are described in which any combination of two anti-receptor molecules that do not compete for the same binding site can be used to detect the cell free T cell antigen receptor. In addition, detection of cell free receptor/complexes may be accomplished in a sandwich immunoassay using an anti-receptor antibody in combination with a second antibody that defines a molecule complexed to the receptor (e.g., the T3 antigen). In the sandwich immunoassays, the sample to be tested is reacted with one antibody which is immobilized. Binding of the sample to the immobilized antibody is assessed by adding the second labeled antibody, herein called the detection antibody, which is directed to a second epitope of the cell free receptor molecule or to the same epitope of a repeating epitope of the cell free receptor. The generation of a bound label or signal indicates the presence of the cell free T cell receptor in the sample. In an alternate embodiment, an anti-receptor antibody and an anti-T cell determinant (e.g. anti-T3) can be used as the immobilized and detection antibodies in order to detect released receptor complexes. Other assay conditions, such as the presence of detergents the types of buffers used, etc. will become apparent to one skilled in the art after reviewing the examples herein.

Methods for quantitatively determining the amount of cell free antigen receptor present in the sample are also provided. To this end any of the immunoassays described above may be accomplished in parallel with a standard containing a known amount of cell free T cell antigen receptor. The amount of reaction complex formed in the standard can be compared to the amount formed in the sample; the amount of cell free antigen receptor can be extrapolated based upon this comparison.

In a particular embodiment of this aspect of the invention we have found that two anti-major framework monoclonal antibodies are quite useful in the identification and detection of released T cell antigen receptors: monoclonal antibodies W4 and beta-F1 (hereinafter referred to as BF1 and which was referred to as 8A3 in parent application Ser. No. 804,289). In most situations, the W4 and BF1 antibodies can be used in either configuration (immobilized or as detection antibodies) to identify and detect the released T cell antigen receptor; however, it appears that the detection of the cell free receptor in sera requires that a particular configuration of these two antibodies be used: immobilized BF1 antibody with W4 detection antibody.

These immunoassays may be used to detect released T cell antigen receptors in a variety of samples such as cell culture, cell lysates, and in patient samples. In addition, these same antibody molecules can be used for immunoaffinity purification and/or enrichment of the released T cell receptor.

5.3. USE OF CELL FREE T CELL ANTIGEN RECEPTOR AND/OR RECEPTOR COMPLEX FOR DIAGNOSIS AND THERAPY

There are at least two approaches to the use of the cell free T cell antigen receptor to the field of diagnostics: (a) the cell free T cell antigen receptor can be used as a detectable marker for disorders or diseases that elicit or involve T cell responses that result in the accumulation of cell free receptors in body fluids; and (b) the cell free T cell antigen receptor itself may be used as a probe directed to a specific disease antigen recognized by the receptor. Each approach offers its own particular advantage.

The use of cell free T cell antigen receptors or receptor/complexes as markers is based upon our discovery that cell free receptors are found at elevated levels in patients with certain disorders or diseases, especially those which elicit or involve T cell responses. As a result, the released T cell antigen receptor may be used as a marker for the diagnosis and monitoring of the disorder or disease. Such disorders or diseases may include, but are not limited to T cell malignancies, autoimmune diseases, transplant/graft rejection, host versus graft disease, cancers, solid tumors, allergies and certain infectious diseases which may be caused by a virus, fungus, parasite or bacterium.

Furthermore, a plurality of T cell clones in an individual can simultaneously respond to more than one pathogen. Thus it is contemplated that the serum from the individual contains a mixture of distinct types of released T cell antigen receptors. The quantitative measurement of each type of the released receptor allows the diagnosis and monitoring of a patient with multiple infections or a disease involving a plurality of pathogens.

Accordingly, patient samples can be tested for the presence and/or amount of released T cell antigen receptor or receptor complex in order to aid diagnosis and disease monitoring. Patient samples to be tested may comprise biological fluids including but not limited to blood, plasma, serum, saliva, urine, spinal fluid, synovial fluid, amnionic fluid and cranial fluid. The amount of released receptor or receptor/complex may be quantitated by running a parallel standard containing a known concentration of the particular receptor or receptor/-complex. Immunoassays using the anti-receptor and other antibodies described herein are particularly useful for this approach. Diagnostic assays which use the cell free or released T cell antigen receptor as a marker offer the advantage of being less invasive to the patient, because body fluids can be tested so as to avoid invasive biopsy techniques.

The use of the cell free T cell antigen receptors or receptor/complexes as diagnostic probes is based upon the ability of the cell free receptors specifically to recognize and bind to particular antigens which are characteristic for certain diseases; these will be referred to as disease-related antigens. This embodiment of the invention involves using the cell free receptor as a probe to detect the disease-related antigens in patient samples in vitro or to identify the location of the disease-related antigens in vivo. Where the disease-related antigen defined by the cell free receptor is released in vivo the patient's body fluids can be tested for the presence and-/or amount of released disease related antigen using the cell free receptors as probes. To this end, the cell free receptors may be appropriately labeled in order to detect reaction complexes formed between the cell free receptors and disease-related antigen in the patient sample. Where the disease-related antigen is not released, the labeled cell free receptors can be used in vivo to localize the disease antigen. In either embodiment, the cell free receptors offer tremendous advantages when diagnosing diseases or disorders characterized by antigens that are not recognized by immunoglobulins. Moreover, where the disease-related antigen is shed or released, noninvasive techniques can be used to assay patient body fluids. Where the disease-related antigen is not shed, the use of released T cell antigen receptors as a diagnostic probe is especially advantageous where the tumor or malignancy is located at a site that cannot be biopsied.

The cell free T cell antigen receptors of the invention may also be used as therapeutic compositions in an admixture with pharmaceutically acceptable carriers. To this end, a cell free T cell antigen receptor that defines a particular antigen and which has a particular effector function (e.g., an immunosuppressive or immunopotentiating effect) may be used at a therapeutically effective dose in the treatment of specific disorders or diseases. For example, cell free antigen receptors which demonstrate immunosuppressive effector functions and which define antigens involved in autoimmune diseases can be used to specifically suppress the autoimmune response directed against that particular antigen. By contrast, antigen receptors which demonstrate immunopotentiating effector functions and which define target antigens on infected cells, cancer cells or tumor cells can be used to specifically provoke and potentiate an immune response directed against that particular cancer or tumor antigen. The cell free antigen receptors, therefore, can be used to modulate immune responses in a target specific fashion and, thus, offer great advantages over therapies which nonspecifically stimulate or suppress the immune system.

Alternatively, toxins and metabolic blocking compounds which kill cells or inhibit growth can be chemically linked to the cell free T cell antigen receptor or fragments or derivatives thereof which are specific for the target cells to be killed. The administration of such compounds at therapeutically effective doses could result in targeted therapy.

Other embodiments of the invention will be further understood by those skilled in the art by reference to the examples which follow.

6. EXAMPLE: DETECTION OF RELEASED T CELL ANTIGEN RECEPTOR AND RECEPTOR COMPLEX

The examples that follow describe various immunoassays that can be used to detect the presence of released T cell antigen in cell free supernatants of T cell cultures, T cell lysates and in human sera. The molecular nature of the released T cell antigen in cell culture and in human sera, as assessed by the characterization of fractions obtained by HPLC gel filtration of such samples is also described. The results indicate that the T cell antigen receptor may be released in a variety of forms, and that the released form may differ from membrane-bound receptors. The detection of elevated levels of released T cell antigen receptor in sera from patients with certain T cell malignancies or infectious diseases is also described. These results indicate that assays which measure serum levels of released T cell antigen may have diagnostic value in monitoring certain T cell malignancies or infectious diseases.

In all the examples that follow, T cell lines and B cell lines, obtainable from the American Type Culture Collection (ATCC) or many university laboratories, were grown and maintained in RPMI 1640 (a culture fluid purchased from Gibco Laboratories, Grand Island, N.Y.) with 10% fetal calf serum at 37° C. and 5% $CO_2$. Culture supernatants were harvested from log growth phase cultures of these cell lines at a cell density of 1 million cells per milliliter. In all cases viabilities were greater than 99%. Supernatants were freed of membrane fragments by centrifugation at 50,000×g for one hour. In some instances an additional step consisting of filtration through a 0.22 um filter (Arco LC13, Gelman Sciences, Ann Arbor, Mich.) was used.

The HPB-ALL T cell line used in the subsections which follow is a widely distributed cell line (for example, see Borst et al., 1986, J. Immunol. 136:601–607; Lanier et al., 1986, J. Immunol. 137: 2286–2292; and Weiss et al., 1986, Proc. Natl. acad. Sci. U.S.A. 83: 6998–7002).

6.1. CELLULAR SPECIFICITY OF ANTIBODIES THAT DEFINE T CELL ANTIGEN RECEPTORS

As previously discussed, there are at least three distinct types of antibodies against T cell antigen receptors, namely, the anti-major framework, anti-minor framework, and anti-clonotypic antibodies (see definitions in Section 3.1. supra). The cellular reactivities of a representative antibody of each type, as measured by immunofluorescence or by immunoprecipitation, are shown in Table I.

TABLE I

REACTIVITY OF CELL LINES WITH DISTINCT TYPES OF ANTI-T CELL ANTIGEN RECEPTOR MONOCLONAL ANTIBODIES*

| Cell Line | Antibody Reactivity* | | |
|---|---|---|---|
| | Anti-Major Framework | Anti-Minor Framework (% positive) | HPB-ALL Anti-Clonotype (% positive) |
| HPB-ALL T cell (leukemia) | + | 80%–100% | 80%–100% |
| Jurkat T cell (lymphoma) | + | 0 | 0 |
| CEM T cell (leukemia) | + | 0 | 0 |
| Peripheral T Cells Of A Normal Subject | + | 1%–5% | 0 |
| Daudi B cell (lymphoma) | − | 0 | 0 |

*The reactivities were studied by cellular immunofluorescence or by immunoprecipitation. Examples of antibodies used:
Anti-clonotypic: Kappler, et al., 1983, Cell 35: 295–302; Boylston, et al., 1984, Eur. J. Immunol. 14: 273; Acuto, et al., 1985, J. Exp. Med. 161: 1326;
Anti-minor framework: Acuto, et al., 1985, J. Exp. Med. 161: 1326; Bigler, et al., 1985, J. Exp. Med. 161: 1450;
Anti-major framework: Brenner, et al., 1984, J. Exp. Med. 160: 541; Spits et al., 1985, J. Immunol. 135: 1922.

In this example, the anti-major framework antibody reacted with all T cells, but not with the B cells. The anti-minor framework antibody reacted with one leukemia (HPB-ALL) T cell line and some peripheral T cells, but not with another lymphoma (Jurkat) T cell line, a leukemic (CEM) T cell line, or a lymphoma (Daudi) B cell line. The anti-clonotypic antibody reacted only with the specific T cell line against which it was raised, i.e. the HPB-ALL T cell line.

Additional experiments were conducted using three anti-major framework antibodies to immunocytochemically stain several established human cell lines. These antibodies, BF1, W4 and W12 were unable to immunoprecipitate the T cell antigen receptor from the surface of Molt 4, a human T cell line which has been shown by flow cytometry to be negative for surface T3/receptor complex. However, immunocytochemical staining of Molt 4 revealed strong reactivity in the cytoplasm with both the anti-major framework antibodies and with anti-T3 antibodies. These results indicate that Molt 4 expresses a cytoplasmic form of the T cell antigen receptor but does not express a membrane bound form.

6.2. T CELL ANTIGEN RECEPTORS RELEASED FROM CULTURED T CELLS

The following experiments were designed and performed to test whether soluble T cell antigen receptors are spontaneously released by cultured T cells. Cell-free supernatants of cultured T cells were assayed for the presence of released T cell receptor using a sandwich immunoassay in which one type of anti-receptor antibody (i.e., either anti-clonotypic, anti-minor framework or anti-major framework) was immobilized. Binding of released T cell receptors present in the culture supernatant to the immobilized antibody was detected by adding a labeled anti-receptor antibody which defines a different epitope of the released T cell antigen receptor (herein referred to as the detection antibody).

The cell-free supernatants to be tested were prepared by harvesting supernatants from log phase cultures. Cells were pelleted by centrifugation at 50,000×g for 1 hour. Membrane fragments were removed by filtering the clarified supernatants through 0.22 um pore size filters.

In order to immobilize anti-receptor antibodies, microtiter plates (Immulon I, purchased from Dynatech, Alexandria, Va.) were coated overnight at 4° C. with one of the anti-receptor antibodies at a concentration of 2.5 ug/ml in phosphate buffered saline (PBS). The next day the plates were treated with 1% bovine serum albumin (BSA) to block any remaining sites on the plate to which protein might be non-specifically absorbed. Plates were then washed with 10 mM Tris pH 8.0 in 0.05% polyoxyethylenesorbitan monolaurate (Tween 20, purchased from Sigma Chemical Company, St. Louis, Mo.).

The, cell-free and membrane-free culture supernatants to be assayed (100 ul aliquots) were diluted with a suitable buffer, e.g., 0.01M Tris, 0.15M NaCl, 1 mM MgCl$_2$, 1 mM phenylmethylsulfonyl-fluoride (PMSF), 10 mM iodoacetamide, 1 ug/ml pepstatin and 10 ug/ml N-tosyl-L-phenylalanine chloromethyl ketone (TCPK), pH 8.0 containing 1% Nonidet P-40 (NP40, polyxyethylene(9)p-tert-octylphenol, an ionic detergent comprising an octyl phenol ethylene oxide condensate containing an average of 9 moles ethylene oxide per molecule, purchased from Sigma Chemical Company). The diluted samples were added to the coated microtiter wells and incubated at 37° C. for two hours. Unbound sample was washed away and 100 ul of a properly titered amount of a biotinylated detection antibody which defined another epitope of the T cell antigen receptor was added. Following a second incubation at 37° C. for two hours, unbound biotinylated detection antibody was washed away and 100 ul of a properly titered amount of a conjugate of streptavidin horseradish peroxidase (purchased from Zymed Laboratories, San Francisco, Calif.) was added and incubated for 30 minutes at 37° C. Unbound conjugate was washed away and freshly made substrate (0.2% OPD, dihydrochloride orthophenylenediamine in buffered peroxide consisting of 0.015% hydrogen peroxide, 65 mM disodium phosphate, 17 mM citric acid pH 5.5) was added. After incubation at 37° C. for 20 minutes, the reaction was stopped by the addition of 50 ul of 2N sulfuric acid and the color which developed in the microtiter well was read at 490 nm (OD 490) on a ELISA reader (MR 600, purchased from Dynatech).

Appropriate controls consisted of: (a) microtiter wells with no immobilized antibody to account for nonspecific binding of the sample to plate; (b) samples from a B cell line or serum from a normal subject to account for nonspecific binding of the immobilized antibody to the sample; and (c) nonrelevant antibodies of the same immunoglobulin isotype of the immobilized and detection antibodies to control for nonspecific binding of either sample to the immobilized antibody or the detection antibody to the plate or sample.

6.2.1. DETECTION OF T CELL ANTIGEN RECEPTOR RELEASED FROM CULTURED T CELLS

The above-described sandwich immunoassay was performed using an anti-minor framework antibody as the immobilized antibody and either an anti-major framework or an HPB-ALL anti-clonotypic antibody as the detection antibody. The cell free supernatants of cultured T cell lines (HPB-ALL, CEM, and Jurkat) as well as Daudi B cell line were assayed either in the presence of 0.1% NP40 or in the absence of detergent.

The results of these assays are shown in Table II below.

TABLE II

DETECTION OF RELEASED T CELL ANTIGEN RECEPTOR

| Source of Culture Supernatant | Detergent Treatment | OD490 Using Immobilized Anti-Minor Framework Antibody and Detection Antibody Indicated:* | |
|---|---|---|---|
| | | Anti-Major Framework | HPB-ALL Anti-Clonotype |
| HPB-ALL T cell line (leukemia) | None | 0.010 | 0.005 |
| | 0.1% NP40 | 0.123 | 0.171 |
| Jurkat T cell line (lymphoma) | None | 0.010 | 0.000 |
| | 0.1% NP40 | 0.014 | 0.019 |
| CEM T cell line (leukemia) | None | 0.006 | 0.005 |
| | 0.1% NP40 | 0.009 | 0.020 |
| Daudi B cell line (lymphoma) | None | 0.007 | 0.000 |
| | 0.1% NP40 | 0.006 | 0.000 |

*Culture supernatants were harvested from log phase cultures and freed of membrane fragments by centrifugation (50,000 × g for 1 hour) and filtration (0.22 um pore size filter). 100 ul of each culture supernatant was analyzed with and without detergent using an anti-minor framework region antibody as the immobilized antibody and an anti-major framework or anti-idiotype antibody as the detection antibody.

From Table II, several conclusions can be drawn. First, the presence of released T cell antigen receptor in the HPB-ALL T cell culture supernatant can be demonstrated only under suitable assay conditions, e.g. when the cell-free supernatants were assayed in the presence of at least 0.1% NP40, a nonionic detergent. Second, the immobilized anti-minor framework antibody is only reactive with the HPB-ALL T cell line, and not with the CEM and Jurkat T cell lines or the Daudi B cell lines. The data in Table II are in accord with the results obtained using the immunofluorescence assay as shown in Table I supra, and confirm the specificity of anti-minor framework antibodies for HPB-ALL T cells because only released receptors from the HPB-ALL leukemia T cells were quantifiable using detection antibodies such as an anti-major framework antibody or an anti-clonotypic antibody in conjunction with immobilized anti-minor framework antibody. These data indicate that the released antigen receptor is related to the membrane antigen receptor.

To determine whether other T cell lines also release T cell antigen receptor, an assay was configured in which the immobilized antibody was an anti-major framework antibody and the detection antibody was a second anti-major framework antibody using the assay conditions previously described. The data shown in Table III indicate that released T cell antigen receptor can be detected using two distinct anti-major framework antibodies in the sandwich immunoassay, provided the immobilized and detection antibodies do not compete for the same binding site.

TABLE III

RELEASED T CELL ANTIGEN RECEPTOR IN CULTURE SUPERNATANTS

| Source of Culture Supernatant | OD490 Using Two Distinct Anti-Major Framework Antibodies as both Immobilized and Detection Antibodies |
|---|---|
| HPB-ALL | 0.401 |
| Jurkat | 0.243 |
| CEM | 0.225 |
| Molt 4 | 0.968 |
| HSB2 | 0.100 |
| Daudi (B Cell) | 0.111 |
| Media Alone | 0.106 |
| Assay Background | 0.076 |

The results in Table III also demonstrate that many T cell lines release anti-major framework reactive antigen receptor into their supernatant. It should be noted that the Molt 4 and CEM cell lines have minimal surface detectable T3 protein. Since T3 and T cell antigen receptor are thought to be coexpressed (Weiss and Stobo, 1984, J. Exp. Med. 160: 1284) one would expect that minimal surface antigen receptor would be detected in these two cell lines. Surprisingly, considerable amounts of T cell antigen receptor were detected in the culture supernatant of these cell lines. This suggests that released T cell antigen receptor may be expressed independently of other T cell determinants that are coexpressed with the cell bound receptor. The results obtained for Molt 4 are particularly surprising because, as previously explained in Section 6.1, the Molt 4 cell line was found to be membrane negative yet cytoplasm positive for T cell receptors. In other words, the Molt 4 cell line expresses. T cell antigen receptors that are restricted to the cytoplasm. These data suggest that the presence or absence of the membrane form of the T cell antigen receptor is not predictive of whether a cell line produces a cell free or released T cell antigen receptor.

Other configurations of the immunoassay are possible; for example, some of the released T cell antigen receptor may be detected by using the same anti-receptor antibody for the immobilized as well as the detection antibody under some conditions, e.g. the existence of a multiplicity of the same antigenic determinant in the receptor preparation. Furthermore, two anti-minor framework antibodies could be used to detect the receptors provided they define distinct or repeating epitopes. It is additionally contemplated that, depending on the nature of the antigenic determinant on the receptor, the type and concentration of a detergent may be important in these assays.

6.2.2. DETECTION OF T CELL ANTIGEN RECEPTOR/T3 PROTEIN COMPLEX RELEASED FROM CULTURED T CELLS

To determine whether at least some of the released T cell antigen receptor is associated with the T3 protein complex, as the membrane-bound receptor has been shown to exist on the T cell membrane (Borst, et al., 1983, J. Biol. Chem. 258:: 5135; Ohashi, et al., 1985, Nature 316: 606), supernatants were assayed using an immobilized anti-T3 antibody (such as OKT3 obtainable from Ortho Diagnostic Systems, Raritan, N.J. or Leu4 obtainable from Becton Dickinson Monoclonal Center, Mountainview, Calif.), and an anti-receptor detection antibody. Supernatants were assayed in the presence or absence of the detergent NP40 or digitonin (purchased from Aldrich Chemical Company, Milwaukee, Wis.) at a final concentration of 0.2%. The results are shown in Table IV below.

TABLE IV

DETECTION OF RELEASED T CELL ANTIGEN RECEPTOR/T3 COMPLEX

| Source of Culture Supernatant | Detergent Treatment* | OD490 Using Immobilized Anti-T3 Antibody and Detection Antibody Indicated: | |
|---|---|---|---|
| | | Anti-Major Framework | HPB-ALL Anti-clonotype |
| HPB-ALL T cell line (leukemia) | None | 0.024 | 0.129 |
| | NP40 | 0.014 | 0.026 |
| | Digitonin | 0.174 | 0.254 |
| Jurkat T cell line (lymphoma) | None | 0.001 | 0.014 |
| | NP40 | 0.003 | 0.017 |
| | Digitonin | 0.128 | 0.036 |
| Daudi B cell line (lymphoma) | None | 0.011 | 0.016 |
| | NP40 | 0.000 | 0.014 |

TABLE IV-continued

DETECTION OF RELEASED T
CELL ANTIGEN RECEPTOR/T3 COMPLEX

| Source of Culture Supernatant | Detergent Treatment* | OD490 Using Immobilized Anti-T3 Antibody and Detection Antibody Indicated: | |
|---|---|---|---|
| | | Anti-Major Framework | HPB-ALL Anti-clonotype |
| | Digitonin | 0.010 | 0.022 |

*Detergent treated supernatants contained a final concentration of 0.2% NP40 or Digitonin as indicated.

Several significant observations are noted from these data. First, the detection of the released T cell antigen receptor complex in the culture supernatant was influenced by the presence of detergents in the assay. In the absence of a detergent, significant amounts of the released receptor complex could be measured in HPB-ALL supernatant using the HPB-ALL anti-clonotype detection antibody. The presence of the detergent digitonin enhanced the detectable level of the released receptor complex in HPB-ALL T cell supernatants as measured by either the anti-major framework or the HPB-ALL anti-clonotype detection antibody. Moreover, the presence of digitonin enabled the detection of the released receptor complex in both T cell lines assayed (i.e., HPB-ALL and Jurkat supernatants) as measured by the anti-major framework detection antibody. By contrast, no complex was detected using either detection antibody in the presence of NP40. Second, when an anti-major framework antibody was used as the detection antibody, the supernatants from both the HPB-ALL and the Jurkat T cell lines were shown to contain released receptor complex. By contrast, when the anti-clonotype detection antibody specific to the HPB-ALL T cell line was used as the detection antibody, only the culture supernatant derived from the HPB-ALL T cell line was shown to contain a significant amount of released receptor complex. In neither mode of detection did the control Daudi B lymphoma cell line give a positive result.

6.2.3. EFFECTS OF DETERGENT TREATMENT ON THE IMMUNO-DETECTION OF RELEASED T CELL ANTIGEN RECEPTOR AND RECEPTOR/T3 PROTEIN COMPLEX

A set of experiments was performed to further investigate the effects of detergent treatment on the detection of released T cell antigen receptor and the effects of using different combinations of antibodies as the immobilized or the detection antibody in the released T cell antigen receptor immunoassay. For this set of experiments different configurations of anti-receptor and anti-T3 antibodies were used to assay HPB-ALL T cell supernatants. The results are shown in Table V.

TABLE V

DETECTION OF RELEASED T CELL ANTIGEN RECEPTOR OR RECEPTOR COMPLEX IN SUPERNATANTS OF HPB-ALL T CELL CULTURES.

| Immobilized Antibody | Detergent* Treatment | OD490 Using Detection Antibody: | | |
|---|---|---|---|---|
| | | HPB-ALL Anti-Clonotype | Anti-minor Framework | Anti-major Framework |
| HPB-ALL Anti-Clonotype | NP40 | 0 | 0.329 | 0.221 |
| | Digitonin | 0 | 0.310 | 0.149 |
| | None | 0.006 | N.D. | 0.011 |
| Anti-Minor Framework | NP40 | 0.540 | 0 | 0.145 |
| | Digitonin | 0.066 | 0 | 0.020 |
| | None | 0.005 | 0.007 | 0.014 |

TABLE V-continued

DETECTION OF RELEASED T CELL ANTIGEN RECEPTOR OR RECEPTOR COMPLEX IN SUPERNATANTS OF HPB-ALL T CELL CULTURES.

| Immobilized Antibody | Detergent* Treatment | OD490 Using Detection Antibody: | | |
|---|---|---|---|---|
| | | HPB-ALL Anti-Clonotype | Anti-minor Framework | Anti-major Framework |
| Anti-T3 | NP40 | 0 | 0 | 0 |
| | Digitonin | 0.251 | 0.167 | 0.216 |
| | None | 0.057 | 0.056 | 0 |

*Detergent treated supernatants contained a final concentration of 0.2% NP40 or Digitonin as indicated.
Nonspecific background readings were subtracted from the values indicated.
N.D. signifies "not done"

As shown in Table V, NP-40 (and not digitonin) enhanced the detection of released T cell antigen receptor when combinations of anti-receptor antibodies were used as the immobilized and detection antibodies in the assay. By contrast, digitonin (and not NP-40) enhanced the detection of released T cell antigen receptor complex when a combination of anti-T3 and anti-receptor antibodies were used as the immobilized and detection antibodies. More specifically, when an anti-minor framework or an HPB-ALL anti-clonotype was used as the immobilized antibody, HPB-ALL supernatant samples treated with NP40 registered a higher level of released T cell antigen receptor than HPB-ALL supernatant samples treated with digitonin. By contrast, when an anti-T3 antibody was used as the immobilized antibody, digitonin treated HPB-ALL supernatants registered a higher level of released T cell antigen receptor complex than the NP40 treated samples. Significant amounts of the released receptor complex could also be detected in the absence of any detergent when immobilized anti-T3 was used in conjunction with an HPB-ALL anti-clonotype or an anti-minor framework detection antibody.

6.2.4. NATURE OF T CELL ANTIGEN RECEPTOR IN CULTURE SUPERNATANTS

In order to show that the T cell antigen receptor measured in culture supernatants was not membrane associated, gel filtration experiments were performed under non-denaturing conditions without detergent. Culture supernatants from HPB and Molt 4 cell cultures of at least $10^6$ cells per ml and greater than 98% viability were harvested. Cells were pelleted at 50,000×g for 1 hour and the clarified supernatants were filtered through a 0.22 um filter. The filtered supernatants were fractionated by HPLC gel filtration as follows: samples were injected into the column using a 250 ul loop into 7.5×300 mm BioSil TSK-250 with 7.5×100 mm BioSil guard column (BioRad Laboratories, Richmond, Calif.) equilibrated in 0.1M phosphate, 0.1M NaCl (pH 6.8) run at 0.5 ml per minute. Absorbance at 280 nm was monitored and 0.25 ml fractions were collected. Columns were calibrated using molecular weight standards supplied by the manufacturer.

Aliquots of 150 ul of each fraction were analyzed for major framework determinants of the released T cell antigen receptor by a modification of the previously described sandwich immunoassay in which two hour incubations at room temperature (20°-25° C.) on a shaker platform (180 rpm) were performed in place of the 2 hour incubations at 37° C.

Figure 1:
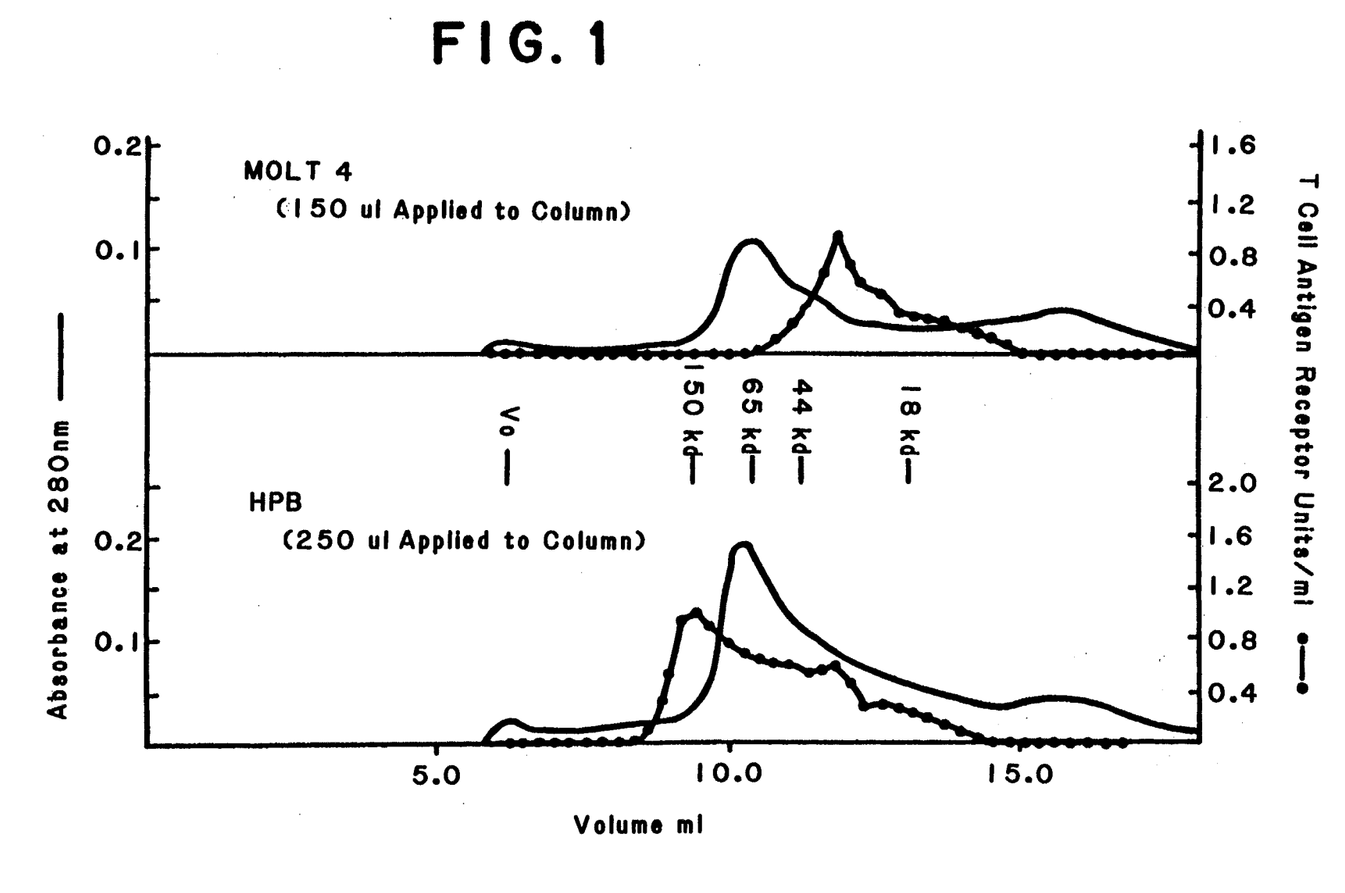
FIG. 1 is a chromatogram indicating molecular size as determined by HPLC gel filtration of released T cell antigen receptors derived from supernatants of T cell line cultures.

The results of this analysis are shown in FIG. 1 which demonstrates that both Molt-4 and the HPB T cell supernatants contained a species characterized by a molecular weight of approximately 40 kd. However, the HPB T cell supernatant contained other species with considerable heterogeneity in size, ranging from apparent molecular weights of 180 kd to 20 kd with the larger forms predominating. In contrast Molt 4 shows only antigen receptor with average apparent weight of 35 kd, suggesting the presence of either a single chain or a fragment of T cell antigen receptor. These results indicate that the T cell antigen receptor may be released in a variety of forms and is not membrane associated.

6.3. DETECTION OF RELEASED T CELL ANTIGEN RECEPTOR IN CELL LYSATES

Cell lysates to be analyzed were prepared from solubilized normal mononuclear or leukemic T cell lines and B cell controls in an isotonic buffer (preferably 0.15M NaCl, 0.01M Tris pH 7.4, 1 mM $MgCl_2$) containing protease inhibitors (preferably PMSF, TCPK, aprotinin, pepstatin, or iodoacetamide) and a detergent (preferably NP40 or digitonin from 0.1 to 5%, more preferably at 1%, although other chemically related detergents will work as well). Following solubilization, nuclei and other debris were pelleted by centrifugation (10 minutes, 400×g followed by recentrifugation at 20 minutes, 50,000×g). Lysates (100 ul aliquots) were analyzed immediately by the ELISA sandwich immuoassay described in the previous examples or stored at 4° C. or frozen for later analysis. It will be apparent to the skilled artisan that tissues could be processed in a similar manner in the case of lymphoid tissue or other tissues infiltrated by lymphocytes (e.g. Mayer, et al., 1985, J. Immunol. 134: 258).

As shown below in Table VI, the solubilized T cell antigen receptor was detected in the cell lysates of the T cell lines and the peripheral mononuclear cells, but not in the B lymphoma cell (Daudi) lysate.

TABLE VI
DETECTION OF T CELL ANTIGEN RECEPTOR IN CELL LYSATES

| Cell Lysate | Cell Equivalents In Assay* (× $10^6$) | OD490 Using Immobilized Anti-Minor Framework Antibody and Anti-Major Framework Detection Antibody |
|---|---|---|
| HPB-ALL T Cell line (leukemia) | 0.250 | 1.577 |
|  | 0.125 | 0.822 |
|  | 0.062 | 0.487 |
|  | 0.031 | 0.233 |
|  | 0.015 | 0.117 |
| Jurkat T Cell line (lymphoma) | 0.250 | 0.020 |
| Peripheral Mononuclear Cells (normal subject)* | 2.000 (0.040) | 0.087 |
|  | 0.500 (0.010) | 0.051 |
|  | 0.125 (0.0025) | 0.019 |
| Daudi B Cell line (lymphoma) | 0.250 | 0.000 |

*Numbers in parentheses indicate the actual cell numbers bearing the anti-minor framework antibody reactivity. It should be noted that the peripheral mononuclear cells contained about 2% cells which were reactive with the immobilized anti-minor framework antibody. Therefore it is necessary to normalize the actual positive cell count so as to compare it with the HPB-ALL T cell line. (See Table I).

A matrix of immobilized antibodies and detection antibodies was performed to investigate the effect of different combinations of antibodies in the measurement of released T cell antigen receptors in NP40 treated HPB-ALL lysates. As shown in Table VII, when the same anti-major framework antibody was used as both the immobilized and detection antibody, a lower but significant level of released T cell antigen receptor could be measured. Similarly, when the same anti-minor framework antibody was used as both the immobilized and detection antibody, a lower but significant level of released T cell antigen receptor could be measured. By contrast, when the same HPB-ALL anti-clonotype antibody was used as both the immobilized and detection antibody, the released T cell antigen receptor could not be detected.

TABLE VII
DETECTION OF T CELL ANTIGEN RECEPTOR IN THE CELL LYSATE OF HPB-ALL T CELLS

| | OD490 Using Detection Antibody*: | | |
|---|---|---|---|
| Immobilized Antibody | HPB-ALL Anti-Clonotype | Anti-Minor Framework | Anti-Major Framework |
| HPB-ALL Anti-Clonotype | 0 | 0.456 | 2.0+ |
| Anti-Minor Framework | 2.0+ | 0.190 | 1.526 |
| Anti-major Framework | 1.543 | 0.969 | 0.550 |

*The cells were lysed with UP40 as previously described herein; 2.5 × $10^6$ cell equivalents were used per assay well.
Nonspecific background readings were subtracted from the values indicated.
+signifies greater than.

The released T cell antigen receptor could also be detected from a number of different cells using two distinct anti-major framework antibodies as the immobilized and detection antibodies. The results in Table VIII demonstrate that using an anti-major framework antibody as the immobilized antibody and a second anti-major framework detection antibody which defines a different epitope of the major framework determinant, T cell antigen receptor can be measured in lysates from a variety of T cell lines and peripheral blood lymphocytes from normal donors but not B cell lines.

TABLE VIII
T CELL ANTIGEN RECEPTOR IN DETERGENT LYSATE FROM T CELL LINES AND PERIPHERAL BLOOD LYMPHOCYTES

| Number of Cells Per Well (× $10^5$) | OD490 of Cell Lysate Using Two Distinct Anti-Major Framework Antibodies as Immobilized and Detection Antibodies* | | |
|---|---|---|---|
| | HPB-ALL T Cell | Jurkat | PBL |
| 10.000 | ND | ND | 0.980 |
| 5.000 | 2.0+ | 2.0+ | 0.689 |
| 2.500 | 2.0+ | 2.0+ | 0.374 |
| 1.250 | 2.0+ | 1.857 | 0.261 |
| 0.625 | 1.505 | 1.069 | 0.155 |
| 0.313 | 0.775 | 0.647 | 0.105 |
| 0.156 | 0.460 | 0.364 | ND |
| | MOLT-4 T Cell | CEM T Cell | |
| 5.000 | ND | 2.0+ | |
| 2.500 | ND | 2.0+ | |
| 1.250 | 2.0+ | 2.0+ | |
| 0.625 | 2.0+ | 2.0+ | |
| 0.313 | 1.897 | 1.562 | |
| 0.156 | 1.029 | 0.867 | |
| 0.078 | 0.633 | ND | |
| 0.039 | 0.345 | ND | |
| | HSB-2 T Cell | Daudi B Cell | |
| 5.000 | 1.455 | 0.096 | |
| 2.500 | 0.966 | 0.097 | |

*Monoclonal antibody W4 was the immobilized antibody and BF1 was the detection antibody. Each monoclonal antibody defines a different epitope of the major framework determinant of the T cell receptor.
ND signifies not done.
+signifies greater than.

T cell antigen receptor complex may be measured in cell lysates from a variety of T cell lines using an anti-T3 antibody as the immobilized antibody and an anti-major framework antibody as the detection antibody under conditions described for T cell antigen receptor-T3 complex in supernatants.

6.4. RELEASED T CELL ANTIGEN RECEPTOR OR RECEPTOR/COMPLEX IN SERA

The presence of released T cell antigen receptor complex in culture supernatants of T cell leukemic lines led us to investigate whether the released antigen receptor complex may be detected in the sera of patients with T cell malignancies or infectious diseases. The experiments described below were designed and performed to confirm this theory.

6.4.1. DETECTION OF RELEASED RECEPTOR/COMPLEX IN SERA OF LEUKEMIC PATIENTS

The following assays were performed using immobilized anti-T3 antibody and anti-major framework detection antibody to determine whether released receptor/complex could be detected in serum samples of leukemic patients.

Microtiter wells from Immulon I plates were coated overnight at 4° C. with an anti-T3 monoclonal or control antibody at 2.5 ug/ml in PBS. The wells were then exhaustively washed, coated with 1% BSA in a buffer containing 0.025M Tris pH 7.4, 0.15M NaCl and 0.05% Tween 20 overnight at 4° C. and exhaustively washed again before the serum sample and T cell lysate were added. Aliquots of serum (50 ul) from leukemic patients or normal subjects were added to the coated wells, mixed with 10 ul of 2% digitonin and 40 ul of fetal calf serum, and incubated at room temperature for 15 minutes. The rest of the assay procedures were performed as described previously. As indicated in Table IX below, serum samples from six patients with T cell leukemia or T cell lymphoma had significantly elevated levels of released T cell antigen receptor complex as compared with the normal subjects.

TABLE IX

RELEASED T CELL ANTIGEN RECEPTOR COMPLEX IN SERA

| Serum Sample | OD490 Using Immobilized Anti-T3 Antibody and Anti-Major Framework Detection Antibody |
|---|---|
| *Patient | |
| A | 0.043 |
| B | 0.506 |
| C | 0.049 |
| D | 0.102 |
| E | 0.053 |
| F | 0.070 |
| **Normal Subject | 0.015 ± 0.0072 |

*Patients A and B were seropositive for human T cell leukemia virus I, and exhibited symptoms of T cell leukemia; Patient C was diagnosed as T cell leukemia; Patients D, E, and F were all diagnosed as T cell lymphoma.
**The average assay value of sera from 16 normal subjects (range of OD490 value: 0.01 to 0.031).

6.4.2. DETECTION OF RELEASED T CELL ANTIGEN RECEPTOR IN SERA OF LEUKEMIC PATIENTS

The following assays were peformed using two distinct anti-major framework antibodies, W4 and BF1 as the immobilized and detection antibodies. A particular configuration of these antibodies appeared to favor the detection of the T cell antigen receptor in the serum samples.

Microtiter wells (Flow Laboratories, McLean, Va.) were coated overnight at 4° C. with an anti-framework monoclonal or control antibody at 4 ug/ml in PBS. The wells were then exhaustively washed, coated with 1% BSA in 0.025M Tris (pH 7.4), 0.15M NaCl and 0.05% Tween-20 at 37° C. for 2 hours. Aliquots of serum (50 ul) from patients and normal subjects (negative controls) or 50 ul of standards consisting of dilutions of an NP40 lysate from HPB T (positive controls) cells were added to the wells followed by 100 ul of a buffer consisting of 50% fetal calf serum, 0.0125M Tris (pH 7.4), 0.075M NaCl, 0.375% NP40, and 100 ug/ml of an irrelevant purified mouse IgG. Samples were incubated at 37° C. for 2 hours, following which unbound sample was washed away. 100 ul of a properly titered HRP conjugate of the second anti-major framework detection antibody was added to each well and incubated an additional 2 hours at 37° C. Wells were washed with PBS 0.05% Tween. 100 ul of the OPD substrate previously described was added, incubated and read in the presence of $H_2SO_4$ as previously described.

Initial results of this assay were unsuccessful at detecting T cell antigen receptor in the serum of adult T cell leukemia (ATL) patients. Furthermore, the recovery of HPB lysate when spiked into serum was relatively low. Reversing the configuration of the antibodies, however, resulted in virtually complete recovery. Using the reversed configuration of the anti-major framework antibodies; i.e., immobilized BF1 followed by W4 detection antibody, the T cell antigen receptor could be detected in these sera (Table X). This is surprising because either configuration of these antibodies can be used successfully to detect T cell antigen released from cultured cells. While the nature of this phenomena in testing sera remains unclear, the correct selection and configuration of antibodies is contemplated to be important in the assay.

TABLE X

DETECTION OF RELEASED T CELL ANTIGEN RECEPTOR IN SERA

| | OD490 of Serum Assayed Using Two Distinct Anti-Major Framework Antibodies as Indicated:* | |
|---|---|---|
| | Immobilized Antibody: | |
| | BF1 | W4 |
| Serum | Detection Antibody: | |
| Sample No. | W4 | BF1 |
| T Cell Leukemia | | |
| #1 | 0.34 | 0.24 |
| 2 | 0.69 | 0.16 |
| 3 | 0.19 | 0.04 |
| 4 | 1.17 | 0.00 |
| 5 | 0.16 | 0.00 |
| 6 | 0.04 | 0.00 |
| 7 | 0.07 | 0.00 |
| 8 | 0.01 | 0.03 |
| 9 | 0.39 | 0.08 |
| 10 | 0.70 | 0.05 |
| Recovery of Cell Lysate Receptor Spiked into Normal Serum | 85% | 30% |

*Nonspecific background readings were subtracted from the values indicated.

6.4.3. NATURE OF T CELL ANTIGEN RECEPTOR IN PATIENT SERA

To compare the nature of T cell antigen receptor in patient sera with the material analyzed in cell culture supernatants HPLC gel filtration was again employed. Sera were diluted 1 to 1 with 0.1M phosphate 0.1M NaCl (pH 6.8) and filtered with a 0.22 um membrane. 250 ul of each sample was injected into the column using conditions as previously described. Assays were performed identically as described for the culture supernatant fractions (Section 6.2.4. supra).

Figure 2:
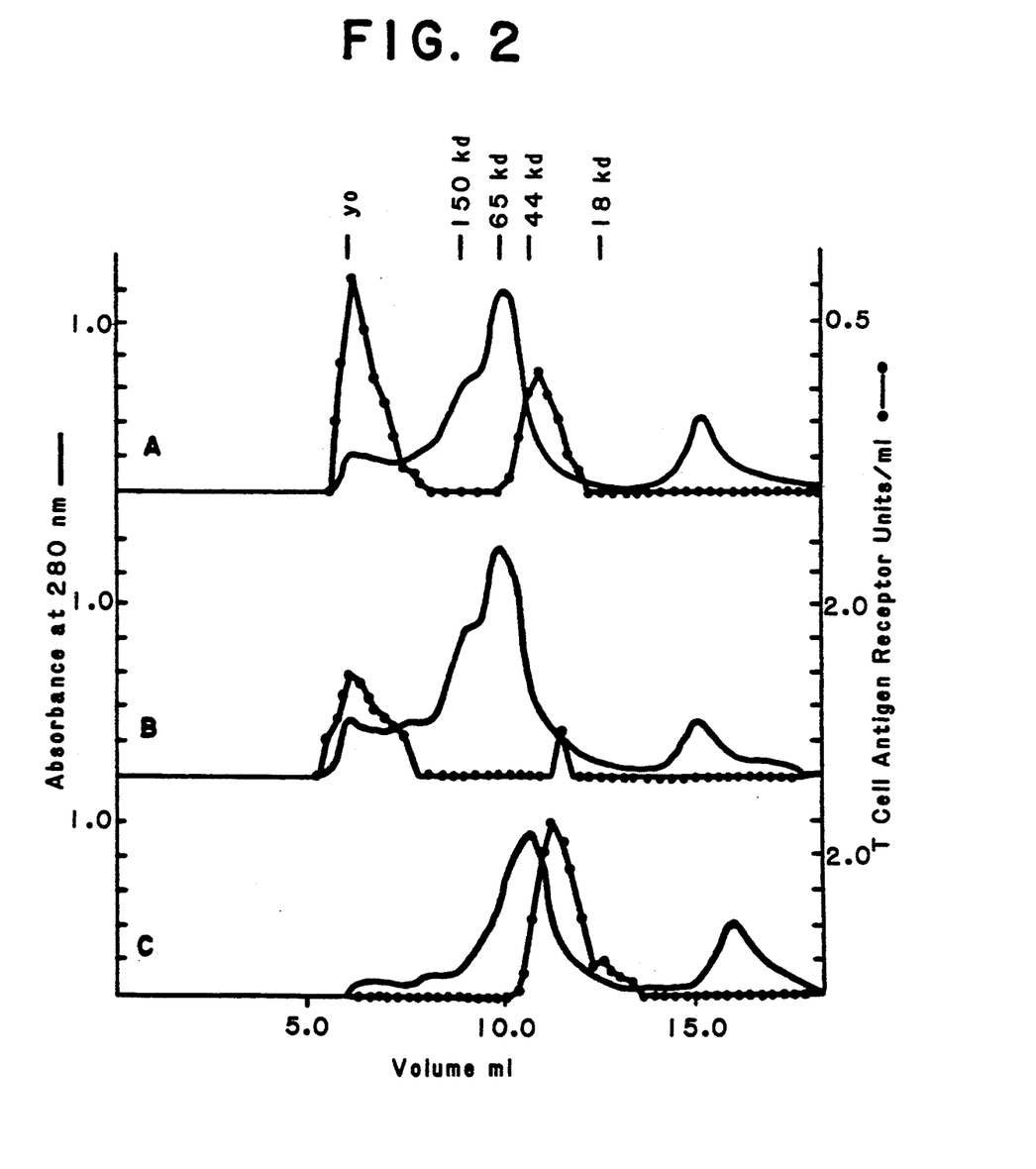
FIG. 2 is chromatogram indicating molecular size as determined by HPLC gel filtration of released T cell antigen receptors in serum from patients with T cell leukemia.

The results of these experiments are shown in FIG. 2 in which A and C represent the chromatograms obtained for patients with acute adult T cell leukemic and B represents the chromatogram for a patient with a T4 chronic lymphocytic leukemia. The data indicate that at least several forms of released T cell antigen receptor may exist in sera and that a different profile may be detected for different patients. The material at the void volume may represent T cell antigen receptor associated with membranes or other molecules or aggregates while the material included within the fractionation range of the column is suggestive of material similar to that seen from the Molt 4 leukemia cell line. These results support the notion that in vivo as well as in vitro T cell antigen receptor may be released in a variety of forms.

6.4.4. DETECTION OF RELEASED T CELL ANTIGEN RECEPTOR IN SERA OF PATIENTS WITH T CELL MALIGNANCIES

Results of assaying 51 leukemic and 8 normal laboratory donors for released T cell antigen receptor in serum samples using the optimized configuration of anti-major framework antibodies are shown in Table XI. Values are expressed, relative to a standard lysate from the HPB T cell line. Normal laboratory donors had no detectable material measured in this assay. Eight of 10 acute ATL patients showed significant levels of antigen receptor. While two of 16 chronic ATL patients showed elevated levels of the released T cell antigen receptor, these data demonstrate that the level of cell free T cell antigen receptor in sera is correlated with disease activity in these ATL patients. Among non ATL leukemic patients, a T4 positive leukemia demonstrated strong reactivity in this assay.

TABLE XI

DETECTION OF RELEASED T CELL ANTIGEN RECEPTOR IN SERA OF PATIENTS WITH T CELL MALIGNANCIES

| Diagnosis | Number of Patients* | Serum Levels of Released T Cell Antigen Receptor (units/ml)** |
|---|---|---|
| Acute Adult T Cell Leukemia | 1 | 79.8 |
| | Patient C | 55.8 |
| | 1 | 55.4 |
| | Patient A | 36.2 |
| | 1 | 32.8 |
| | 1 | 21.0 |
| | 1 | 17.4 |
| | 1 | 4.6 |
| | 3 | 2.0— |
| Chronic Adult T Cell Leukemia | 1 | 72.8 |
| | 1 | 29.8 |
| | 8 | 2.0— |
| Smoldering Adult T Cell Leukemia | 1 | 16.8 |
| | 1 | 3.6 |
| | 7 | 2.0— |
| Non Adult T Cell Leukemia | Patient B | 104.2*** |
| | 1 | 14.0 |
| | 1 | 12.0 |
| | 1 | 11.4 |
| | 1 | 4.6 |
| | 5 | 2.0— |
| Normal | 10 | 2.0— |

*Patients A, B and C correspond to A, B and C in FIG. 2.
**Serum levels were assayed by the optimized sandwich immunoassay in which immobilized BF1 and W4 detection antibodies were employed. Units are expressed relative to the readings obtained from a standard HPB T cell lysate which served as the positive control.
***This sample was taken from a patient with T4 chronic lymphocytic leukemia.
—signifies less than.

It is contemplated that the level of released T cell antigen receptor may have diagnostic value in the monitoring of T cell related malignancies.

6.4.5. DETECTION OF RELEASED T CELL ANTIGEN RECEPTOR IN SERA OF PATIENTS WITH INFECTIOUS DISEASE

Results of assaying for released T cell antigen receptor in sera of patients with infectious diseases are shown in Table XII. Significant levels of released T cell antigen receptors are also seen in patients with herpesvirus infection. It is possible that this material may be released directly due to the disease or due the immune reaction to the disease. In either event, it is contemplated that the level of released T cell antigen receptor may have a diagnostic value in monitoring infectious diseases.

TABLE XII

DETECTION OF RELEASED T CELL ANTIGEN RECEPTOR IN SERA OF PATIENTS WITH INFECTIOUS DISEASE

| Diagnosis | Number of Patients | Serum Levels of Released T Cell Antigen Receptor (units/ml)* |
|---|---|---|
| Epstein Barr Virus Infection | 1 | 140 |
| | 1 | 100 |
| | 1 | 76 |
| | 1 | 66 |
| | 1 | 50 |
| | 1 | 37 |
| | 1 | 33 |
| | 1 | 31 |
| | 1 | 25 |
| | 1 | 20.6 |
| | 1 | 13.4 |
| | 1 | 11 |
| | 1 | 2.0— |
| Cytomegalovirus Infection | 1 | 48 |
| | 1 | 30 |
| | 1 | 26 |
| | 1 | 10 |
| | 2 | 2.0— |
| Normal Blood Donor | 2 | 20.0 to 21.0 |
| | 1 | 8.5 |
| | 2 | 7.0 to 7.5 |
| | 4 | 6.0 to 6.5 |
| | 5 | 5.0 to 5.5 |
| | 2 | 4.0 |
| | 2 | 3.0 to 3.5 |
| | 5 | 2.0 to 2.5 |
| | 1 | 1.0 |
| Normal Laboratory | 5 | 2.0— |

TABLE XII-continued

DETECTION OF RELEASED T CELL ANTIGEN RECEPTOR IN SERA OF PATIENTS WITH INFECTIOUS DISEASE

| Diagnosis | Number of Patients | Serum Levels of Released T Cell Antigen Receptor (units/ml)* |
|---|---|---|
| Workers | | |

*Serum levels were assayed by the optimized sandwich immunoassay in which immobilized BF1 and W4 detection antibodies were employed. Units are expressed relative to the readings obtained from a standard HPB T cell lysate which served as the positive control.
—signifies less than.

7. DEPOSIT OF MICROORGANISMS

The following hybridomas have been deposited with the American Type Culture Collection, Rockville, Md., and have been assigned the listed accession numbers:

| Hybridoma | Antibody Type | Accession Number |
|---|---|---|
| W4 | Anti-major framework | HB 9282 |
| BF1 | Anti-major framework | HB 9283 |

The present invention is not to be limited in scope by the embodiments disclosed in the examples which are intended as illustration of a few aspects of the invention and any methods which are functionally equivalent are within the scope of this invention. Indeed, various modifications of the invention in addition to those shown and described herein will become apparent to those skilled in the art and are intended to fall within the scope of the appended claims.

What is claimed is:

1. An isolated molecule purified from the cell free portion of a cell culture or biological fluid, which molecule:
   (a) is released from a T cell:
   (b) is an extracellular molecule not associated with a T cell membrane;
   (c) has an antigenic determinant of a T cell antigen receptor beta chain and,
   (d) exists as a monomer having an average apparent molecule weight of 35–40 KD as measured by HPLC gel filtration in said culture or fluid.

2. The molecule of claim 1 which contains an epitope of the T cell antigen receptor selected from the group consisting of a constant region, a variable region, and a hypervariable region.

3. The molecule of claim 1 reactive with monoclonal antibody W4 produced by a hybridoma deposited with the ATCC having accession number HB 9282.

4. The molecule of claim 1 reactive with monoclonal antibody BF1 produced by a hybridoma deposited with the ATCC having accession number HB 9283.

5. The molecule of claim 1 reactive with two monoclonal antibodies, W4 and BF1, produced by hybridomas deposited with the ATCC having accession numbers HB 9282 and HB 9283, respectively.

6. The molecule of claim 1 in which said biological fluid is human serum.

7. An isolated molecule, purified from the cell free portion of a cell culture or biological fluid, which molecule:
   (a) is released from a T cell;
   (b) is an extracellular molecule not associated with a T cell membrane;
   (c) has an antigenic determinant of a T cell antigen receptor beta chain; and
   (d) exists as a monomer having an average apparent molecular weight of 35–40 KD as measured by HPLC gel filtration in said culture or fluid;

which isolated molecule further reacts positively in the following sandwich immunoassay comprising the steps of:
   (i) contacting the cell free portion with an immobilized monoclonal antibody BF1 as produced by a hybridoma deposited with the ATCC having accession number HB 9283, under conditions which allow immunospecific binding;
   (ii) removing unbound substances;
   (iii) adding a labeled W4 detection antibody, as produced by a hybridoma deposited with the; ATCC having accession number 9282, to the reaction mixture of step
   (i) under conditions which allow immunospecific binding;
   (iv) removing unbound substances; and
   (v) detecting whether immunospecific binding has occurred in the reaction mixture of step (iii).

8. The molecule of claim 7 in which said biological fluid comprises human serum.

* * * * *